United States Patent [19]

Hassler

[11] Patent Number: 5,025,789
[45] Date of Patent: Jun. 25, 1991

[54] SHOCK WAVE SOURCE HAVING A CENTRAL ULTRASOUND LOCATING SYSTEM

[75] Inventor: Dietrich Hassler, Uttenreuth, Fed. Rep. of Germany

[73] Assignee: Siemens Aktiengesellschaft, Berlin and Munich, Fed. Rep. of Germany

[21] Appl. No.: 250,522

[22] Filed: Sep. 29, 1988

[30] Foreign Application Priority Data

Oct. 19, 1987 [DE] Fed. Rep. of Germany ....... 3735346

[51] Int. Cl.⁵ .............................................. A61B 17/22
[52] U.S. Cl. .......................... 128/660.03; 128/24 EL
[58] Field of Search ............... 128/24 A, 328, 660.03, 128/660.1, 662.03, 663.01; 73/644; 606/127–128

[56] References Cited

U.S. PATENT DOCUMENTS

| | | | |
|---|---|---|---|
| 4,080,839 | 3/1978 | Shraiber et al. | |
| 4,155,259 | 5/1979 | Engeler | 128/661.01 |
| 4,246,791 | 1/1981 | Glenn | 128/660.1 |
| 4,271,706 | 6/1981 | Ledley | 128/661.01 |
| 4,281,550 | 8/1981 | Erikson | 128/661.01 |
| 4,294,119 | 10/1981 | Soldner | 128/661.01 |
| 4,333,474 | 6/1982 | Nigam | 128/660.1 |
| 4,339,952 | 7/1982 | Foster | 128/915 |
| 4,382,290 | 5/1983 | Havira | |
| 4,385,255 | 5/1983 | Yamaguchi et al. | 128/662.03 |
| 4,398,539 | 8/1983 | Proudian | 128/661.01 |
| 4,399,703 | 8/1983 | Matzuk | 128/660.1 |
| 4,545,385 | 10/1985 | Pirschel | 128/915 |
| 4,552,021 | 11/1985 | Miwa et al. | 73/644 |
| 4,610,249 | 9/1986 | Makofski et al. | 128/328 |
| 4,617,931 | 10/1986 | Dory | 128/24 EL |
| 4,658,828 | 4/1987 | Dory | 128/660.03 |
| 4,762,002 | 8/1988 | Adams | 128/660.1 |
| 4,771,787 | 9/1988 | Wurster et al. | 128/328 |
| 4,844,079 | 7/1989 | Naser | 128/24 EL |

FOREIGN PATENT DOCUMENTS 3328068 2/1985 Fed. Rep. of Germany .

OTHER PUBLICATIONS

"Annular Array Transducer for Deep Acoustic Hyperthermia," Do-Huu et al., 1981, Ultrasonics Symposium, pp. 705–710.

"A Stacked Linear Phased Array Applicator for Ultrasonic Hyperthermia," Ocheltree et al., 1984, Ultrasonics Symposium, pp. 689–692.

Primary Examiner—Lee S. Cohen
Assistant Examiner—John D. Zele
Attorney, Agent, or Firm—Hill, Van Santen, Steadman & Simpson

[57] ABSTRACT

A shock wave source for use in lithotripsy has an electromagnetic shock wave source with the ultrasound head of an ultrasound locating system centrally disposed within the source. During locating of a calculus to be disintegrated, at least one surface normal of the exit face of the ultrasound head is aligned obliquely relative to the surface normal of the coupling surface of the shock wave source. Image disturbances due to multiple echoes are avoided by the oblique positioning of the ultrasound exit face.

16 Claims, 5 Drawing Sheets

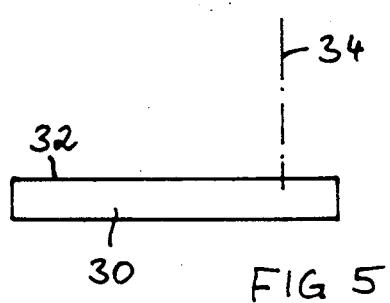 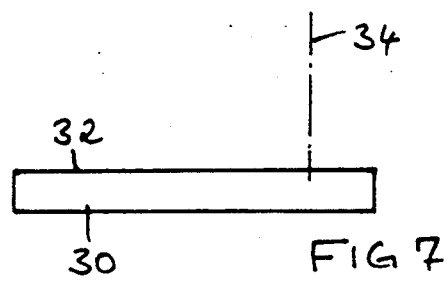
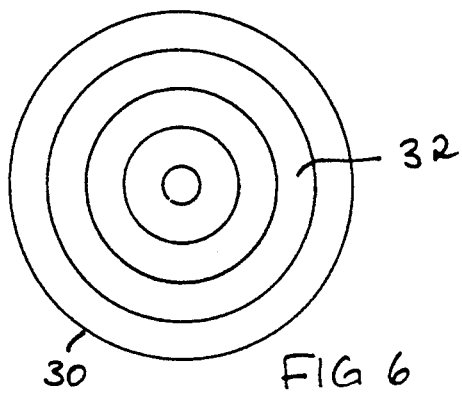 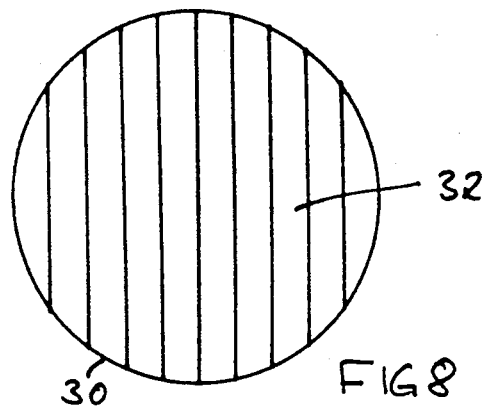
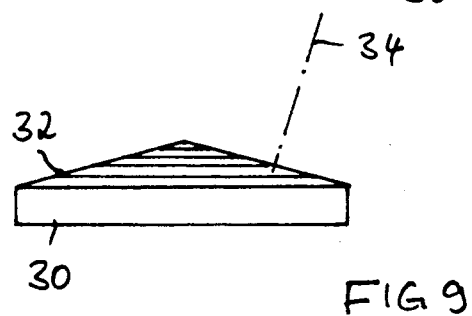
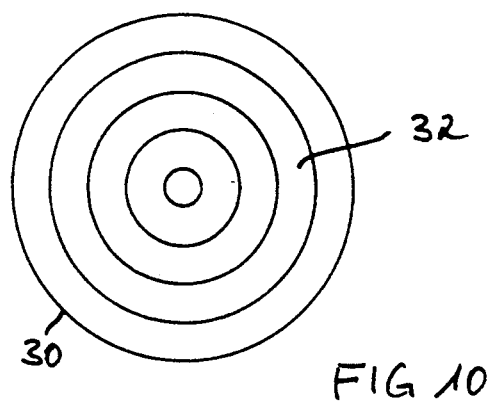

5,025,789

SHOCK WAVE SOURCE HAVING A CENTRAL ULTRASOUND LOCATING SYSTEM

BACKGROUND OF THE INVENTION

1. Field of the Invention

The present invention is related to a shock wave source suitable for use in lithotripsy, and in particular to such a shock wave source having a central ultrasound locating system.

2. Description of the Prior Art

An electromagnetic shock wave source for noncontacting disintegration of a calculus in the body of a patient is disclosed in German OS 33 28 068. The shock wave source has an ultrasound head of ultrasound locating equipment disposed therein, the ultrasound head serving as an ultrasound transmission and reception means for locating and observing a calculus. The ultrasound head is located next to, or between, a number of shock wave sources. It is a disadvantage of this conventional arrangement that the lateral placement of the ultrasound head occupies additional structural space.

A further disadvantage, given the stationary ultrasound head as shown, for example, in FIG. 1 of the above document, multiple reflections between the ultrasound head and the application location result because of unavoidable mis-matchings in the media through which the ultrasound signals must pass. If the received echoes of these multiple reflections are exactly incident on the imaging location of the calculus on the monitor of the ultrasound locating system, locating and observation of the calculus is noticeably disturbed.

It is proposed in German Patent Application P37 27 691.3 corresponding to copending application U.S. Ser. No. 869,501, filed May 30, 1986, which is a continuation-in-part of U.S. Ser. No. 633,828, filed July 24, 1984 (Pauli and Reichenberger), that a central opening be provided in a shock wave source operating according to the electromagnetic principle, with an ultrasound locating system introduced into this opening during operation of the ultrasound head. It is still possible in this system, however, that multiple reflections may arise resulting in echoes which fall exactly onto the location of the calculus image.

SUMMARY OF THE INVENTION

It is an object of the present invention to provide a shock wave source for a lithotripsy system having an ultrasound locating system wherein an exact observation and/or localization of the calculus can be achieved, given a stationary ultrasound head.

It is a further object of the present invention to provide such a shock wave source which is compact in structure.

The above object is achieved in accordance with the principles of the present invention in a shock wave source having a central opening in which an ultrasound head is received, with at least one surface normal of the exit face of the ultrasound head being disposed obliquely relative to the surface normal of the application surface of the shock wave source during locating using the ultrasound system.

In one embodiment of the invention, the ultrasound exit fact of the ultrasound head is planar. The ultrasound head is preferably a linear array or a phased array.

In a further embodiment, the exit face of the ultrasound head is conical, in which case the ultrasound head is preferably an annular array. The ultrasound head may be pivotable around an axis disposed in the base region of the conical portion of the ultrasound head. During shock wave operation, the ultrasound head is pivoted about this axis to a position in which the ultrasound head only slightly shadows the pressure pulses of the shock wave source.

DESCRIPTION OF THE DRAWINGS

FIGS. 5 and 6 respectively show side elevational and plan views of a planar ultrasound head having an annular transducer array.

FIGS. 7 and 8 respectively show side elevational and plan views of a planar ultrasound head having a side-by-side transducer array.

FIGS. 9 and 10 respectively show side elevational and plan views of a conical ultrasound head having an annular transducer array.

DESCRIPTION OF THE PREFERRED EMBODIMENTS

Figure 1:
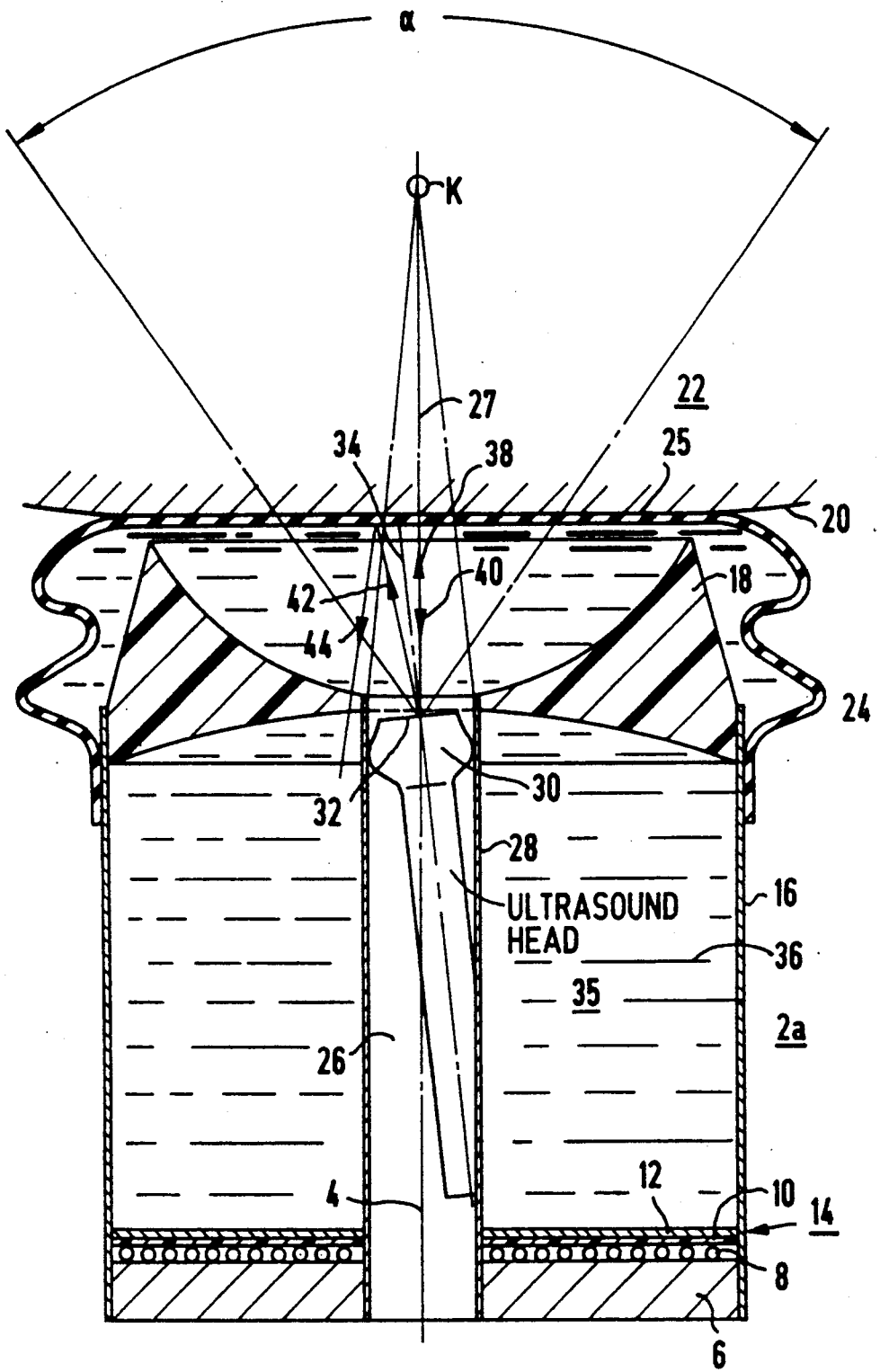
FIG. 1 is a longitudinal section through a shock wave source having an ultrasound head in the form of a linear array, constructed in accordance with the principles of the present invention.

In FIG. 1, a shock wave source operating according to known electromagnetic principles is generally referenced 2a. The shock wave source 2a is axially symmetrical relative to a central axis 4, and thus has the exterior shape of a cylinder. A coil carrier 6 having a flat coil 8 thereon is disposed at one end of the shock wave source 2a. An insulating foil 10 is attached to the flat coil 8 at the side thereof opposite the coil carrier 6, preferably by gluing.

A metallic membrane 12 is disposed immediately adjacent the insulating foil 10. The intimate contact between the insulating foil 10 and the membrane 12 can be produced by under-pressure in a known manner.

The coil carrier 6, the flat coil 8, the insulating foil 10 and the membrane 12 form a core 14 of the shock wave source 2a. The core 14 is disposed at one end of a tubular housing 16, and terminates the housing 16 at that end. A focusing element 18 is mounted at or near the opposite end of the housing 16. The focusing element 18 focuses the acoustic pulses or shock waves of the shock wave source 2a onto a calculus K in the body of a patient 22. A flexible sack 24 is secured at the exterior of this end of the housing 16 in liquid-tight fashion. The flexible sack 24 couples shock waves to the skin surface 20 of the patient 22 with low losses. For matching the shock wave source 2a to the calculus K, which is at a certain depth within the patient 22, the coupling sack 24 is in the form of an accordion bellows. The application surface 25 is planar. A surface normal 27 of the application surface 25 is aligned parallel to the central axis 4.

A cylindrical volume 26 is disposed centrally in the shock wave source 2a, the volume 26 being substantially free of the acoustic pulses generated by the core 14 during a shock wave generating mode. The volume 26 is limited by, or lined with, a tube 28, having one end secured in the focusing element 18, and its opposite end secured in the core 14. The longitudinal axis of the volume 26 is coincident with the central axis 4. An ultrasound head 30 of an ultrasound locating system (the remainder of which is not shown) is stationarily mounted and fixed liquid-tight in the volume 26. In the embodiment of FIG. 1, the ultrasound head 30 is a linear array or a phased array (electronic sector scanner). The ultrasound head 30 has an ultrasound exit face 32 which is planar, and is disposed close to the focusing element 18. A surface normal 34 of the ultrasound exit face 32 forms a selected angle relative to the central axis 4, which differs from zero. The surface normal 34 will thus also form an angle other than zero with the surface normal 27 of the coupling face 25, and the skin surface 20. In other words, the exit face 32 will not lie parallel to the skin surface 20.

The interior 35 of the shock wave source 2a is limited by the membrane 12, the housing 16, and the sack 24, as well as by the wall 28 and the sides of the ultrasound head 30. The interior 35 is filled with a coupling liquid 36, which is a shock wave conducting medium. The shock wave source 2a may be accommodated with compensating vessels which receive or deliver the coupling liquid 36 to and from the interior 35 so that the position of the shock wave source 2a can be matched to different calculi K disposed at different depths within the body 22. Such compensating vessels are known in the art, and are not specifically shown. Mechanical mounting and fixing elements for the shock wave source 2a, as are also known in the art, may be provided as well, but are not shown in the drawings. The acoustic properties of the coupling liquid 36, which may be, for example, water, substantially correspond to those of the patient 22.

Multiple reflections between the exit face 32 and the coupling sack 24, as well as the skin surface 20, are avoided by the oblique alignment of the normal 34 of the ultrasound exit face 32 relative to the central axis 4. Such multiple reflections are particularly disturbing if the received echo signals deriving therefrom coincide with the location of the calculus K in the displayed image, i.e., when the distance between the ultrasound exit face 32 and the calculus K is a whole multiple of the distance between the ultrasound exit face 32 and the skin surface 20.

The path of a reflected ultrasound beam is as described below. An ultrasound transmission pulse will be considered which is emitted by the ultrasound head 30 in the direction of the central axis 4. This is illustrated by the arrow 38. As a consequence of the unavoidable acoustic mismatching, this transmission pulse is partially reflected by the skin surface 20 and/or by the coupling sack 24 back in the direction of the central axis 4, as illustrated by the arrow 40. Because the reflected pulse is now incident on the ultrasound exit face 30 at an angle relative to the surface normal 34 which differs from zero, it is at least partially reflected again with the same angle relative to the surface normal 34. This is indicated by the arrow 42. Because the reflected beam is now no longer perpendicularly incident at the skin surface 20 or the coupling face 25 of the coupling sack 24, it is reflected at the surfaces 20 and 25 under the condition of an angle of incidence equal to the exit angle. The ultrasound pulse reflected for the second time at the skin surface 20, or at the coupling sack 24, is now no longer incident on the ultrasound exit face 32, and simply passes into the coupling liquid 36. Thus only a first reflection 40 of the ultrasound pulse will again be incident on the ultrasound exit face 32. The echo signal of the first reflection 40 indicates the position of the skin surface 20 on the display monitor.

Figure 2:
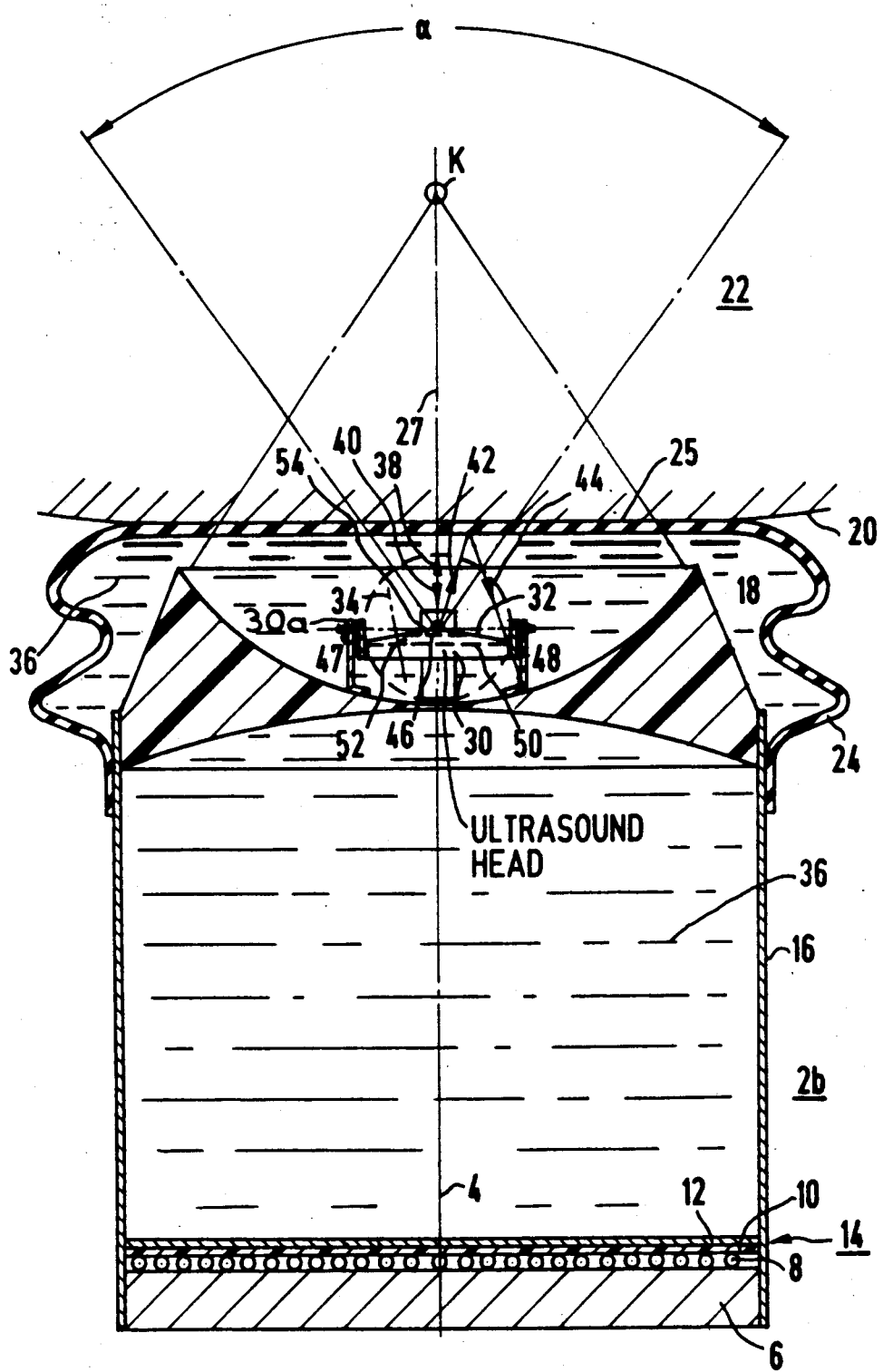
FIG. 2 is a longitudinal section of a shock wave source having an ultrasound head in the form of an annular array, constructed in accordance with the principles of the present invention.

The shock wave source 2b shown in FIG. 2 is constructed similar to the shock wave source 2a in FIG. 1. Identical components are identified with the same reference symbols. The shock wave source 2b differs from the shock wave source 2a in the structure and arrangement of the ultrasound locating system. The volume 26, which is free of acoustic pulses in the shock wave source 2a, is absent in the embodiment of FIG. 2.

The ultrasound head 30 of the ultrasound locating system in the embodiment of FIG. 2 is supported in a mount 30a so as to be rotatable around an axis 46, in the volume between the outer limiting face of the focusing element 18 and the flexible sack 24. The axis 46 is disposed perpendicularly relative to the central axis 4 as shown in FIGS. 9 and 10. The ultrasound head 30 is, in this embodiment, a ring or annular array, having a conical ultrasound exit face 32. The divergent effect of the conical ultrasound exit face 32 is compensated by a corresponding electronic drive of the individual rings. The ultrasound head 30 oscillates around the axis 46 during locating and observation of the calculus K. A scan sector is taken using electronic focusing.

In order that the acoustic pulses emanating from the shock wave source 2b are not unnecessarily shadowed (blocked) by the ultrasound head 30, the ultrasound head 30 is pivoted to a position during activation of the shock wave source 2b so that shadowing of the shock waves is minimal.

The ultrasound head 30 is pivotable around a further axis 47, either manually or driven by a motor. The axis 47 is disposed perpendicularly on the surface containing the central axis 4 and the axis 46. The scan sector α can thus be laterally dislocated. It is thus possible to scan not only a sectional surface, but also a volume, using this ultrasound locating system. This is a particular advantage if the position of the calculus K to be treated has not yet been precisely identified. The position of the calculus can be identified without moving the shock wave source 2b toward the coupling surface 25. The central axis 4 is then subsequently aligned with the calculus K.

Figure 4:
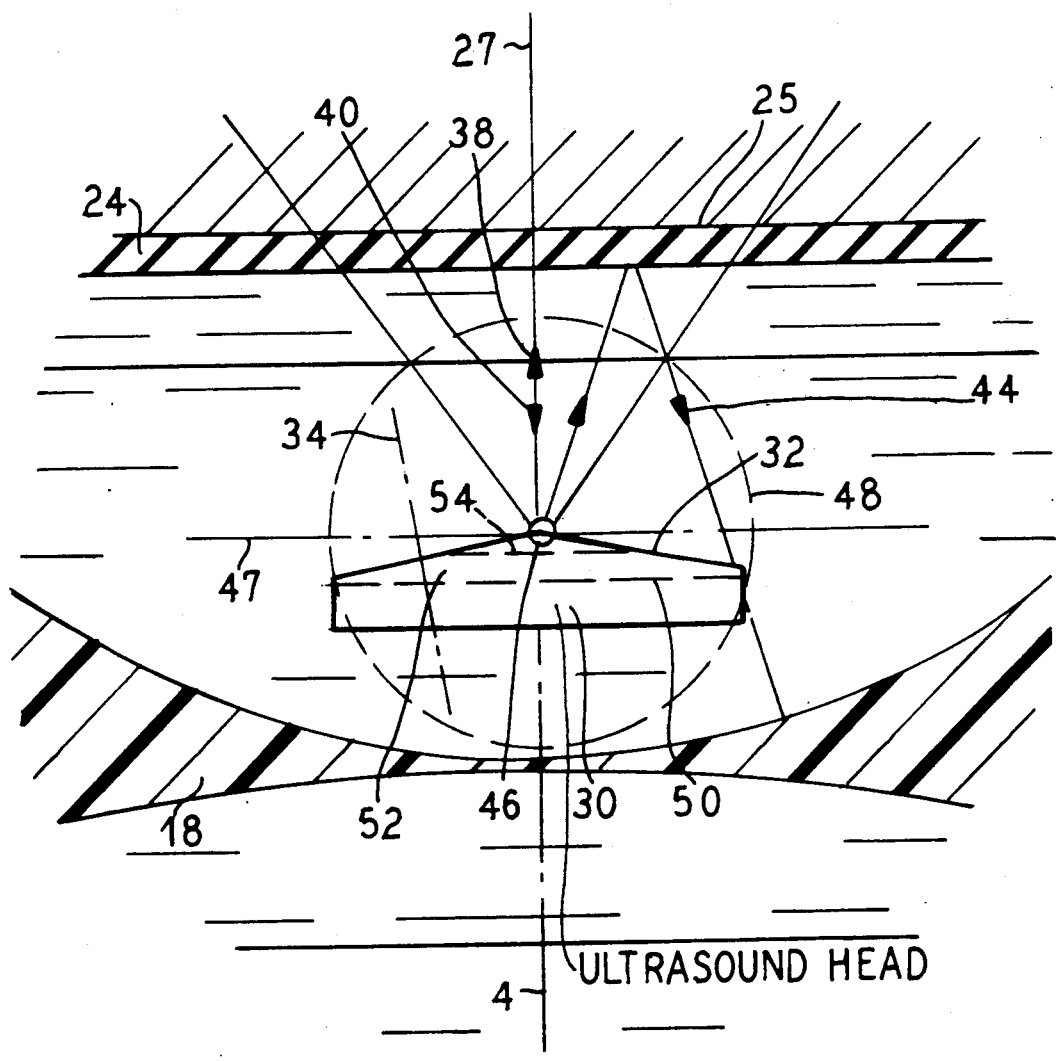
FIG. 4 is an enlarged view of the region surrounding the ultrasound head in the shock wave source of FIG. 2.

The region surrounding the ultrasound head 30 in the embodiment of FIG. 2 is shown enlarged in FIG. 4, without the mount 30a, for clarity.

Because the ultrasound head 30 is mounted so as to be pivotable at the tip of its conical ultrasound exit face, the diameter of the rotational circle described as it pivots about the tip (indicated by the dashed line 48) is of approximately the same size as the diameter of the ultrasound head 30 itself. The largest possible aperture of the ultrasound head 30 is obtained when the axis 46 lies in a base area 50 of a conical part 52 of the ultrasound head 30. The conical part 52 of the ultrasound head 30 is limited by the base 50, and by the conical ultrasound exit face 32. Large apertures can also be achieved if the axis 46 is situated in a circular sectional surface 54, which lies between the tip of the conical part 52 and the base 50.

The conical ultrasound exit face 32 also prevents disturbing multiple reflections in the manner described earlier. An emitted ultrasound locating pulse is again identified by the arrow 38. This pulse is partially reflected at the skin surface 20 and/or at the coupling sack 24 because of the unavoidable acoustic mis-matchings. The direction of the reflected pulse coincides with the direction of the transmitted pulse, as indicated by the arrow 40. The reflected beam is incident on the conical ultrasound exit face 32. Because the direction of the incident pulse does not coincide with the surface normal 34, (see FIG. 9) the beam is reflected in the direction of the arrow 42 by the exit face 32 in accordance with the law that the angle of incidence equals the exit angle. After the second reflection at the skin surface 20 and/or at the coupling sack 24, indicated by the arrow 44, the ultrasound locating pulse no longer is incident on the active surface of the ultrasound head 30. The first reflection 40 indicates the position of the skin surface 20 on a display monitor of the ultrasound locating system.

Figure 3:
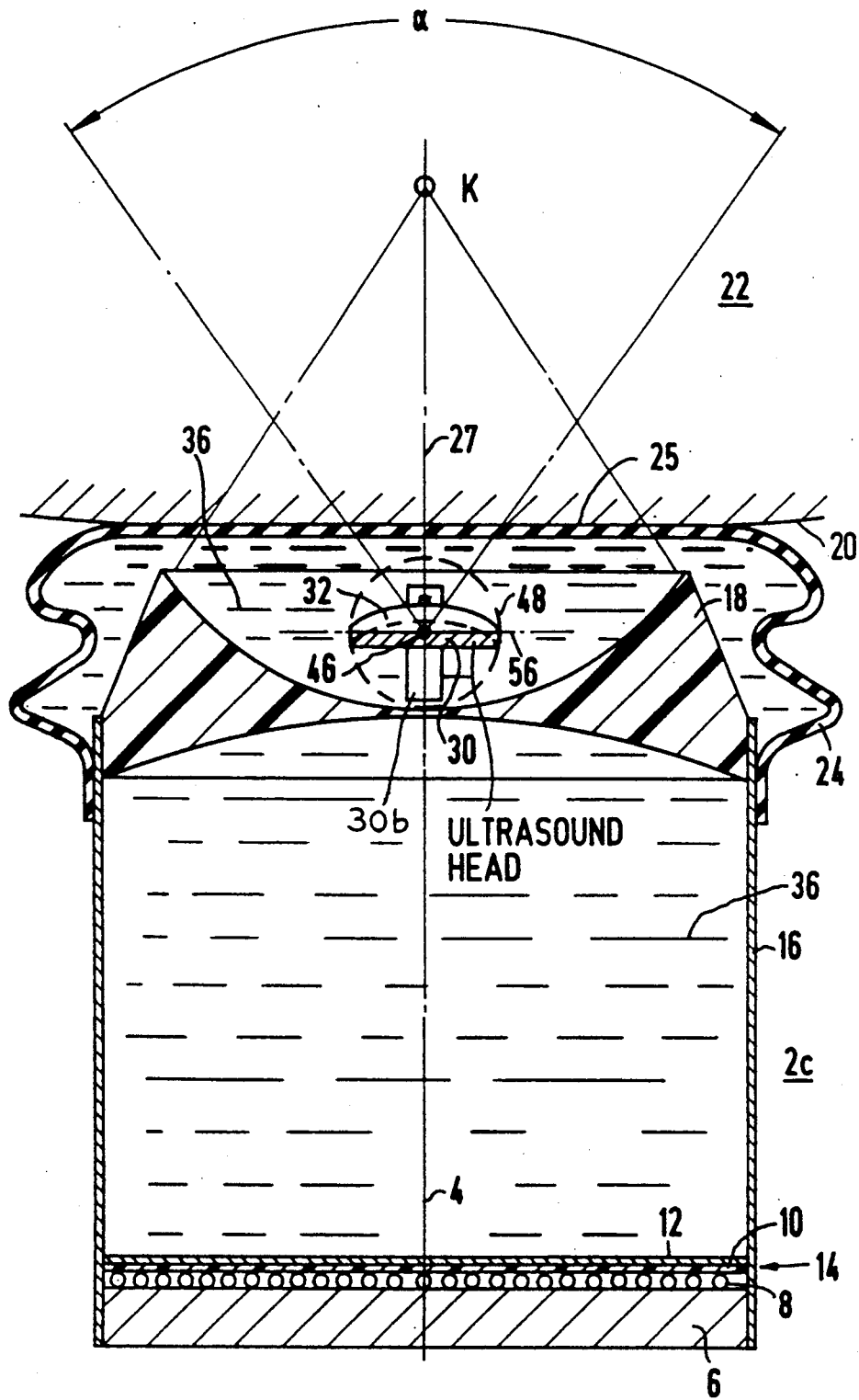
FIG. 3 is longitudinal section of a shock wave source having an ultrasound head in the form of a planar annular array, constructed in accordance with the principles of the present invention.

In a further embodiment of the invention shown in FIG. 3, the ultrasound exit face 32 is planar. The structure of the shock wave source 2c shown in FIG. 3 is similar to that of FIG. 2, with identical reference symbols being used for identical components.

In the embodiment of FIG. 3, the ultrasound head is of uniform thickness, and is cylindrical. The ultrasound head 30 is supported in a mount 30b so as to be pivotable around an axis 56 disposed perpendicularly to the central axis 4, as well as around the axis 46 so that a surface normal 34 (see FIG. 7) of the exit face 32 forms an angle with the central axis 4 which differs from zero. The ultrasound head in the embodiment of FIG. 3 is a linear array as shown in FIGS. 7 and 8. The individual transducers of the ultrasound head are disposed successively side by side in the direction of the axis 46 (one such transducer being seen in side section in FIG. 3). The oblique alignment of the exit face 32 is compensated by appropriate electronic drive of the transducers comprising the ultrasound head 30. Scanning ensues in a plane which contains the central axis 4. As in the embodiments described in connection with FIGS. 1 and 2, multiple reflections are avoided in the embodiment of FIG. 3. Only the echo of the first reflection of an ultrasound pulse emitted along the central axis 4 will again be incident on the active surface, i.e., on the exit face 32. Subsequent reflections at the skin surface 20 and/or at the coupling sack 24 miss the ultrasound head. The further details of the structure and operation of the shock wave source 2c are the same as for the shock wave source 2b of FIG. 2.

In the embodiment of FIG. 3, the transducer array may alternatively be planar, but with an annular configuration, as shown in FIGS. 5 and 6.

In the embodiment of FIG. 1, the ultrasound head 30 of the phased array is not brought to the coupling sack 24, but rather is disposed at a given distance from the coupling sack 24 in an opening of the focusing element 18. Shadowing of the shock wave pulse thus is slight. Image disturbances due to multiple echoes are avoided by the oblique positioning of the ultrasound exit face.

In the embodiments of FIGS. 2 and 3, making use of a mechanical sector scanner which is electronically focused (annular array consisting of individual transducer elements so as to effect an off-axis scan or linear array), shadowing is maintained at a minimum by pivoting the transducer 30 away from the propagation direction of the shock wave pulses. As explained above, the conical or obliquely directed ultrasound exit face 32 prevents disturbances from occurring in the image due to multiple echoes.

In lithotripsy devices having a shock wave generator with a centrally disposed ultrasound locating system, as disclosed herein, which can be used for disintegrating kidney stones or gallstones, the ultrasound access path to the calculus K is the same as the path for the shock waves. Multiple reflections which can disturb observation and locating of the calculus K are avoided by the oblique alignment of the exit face 32. An image of the region under observation which is free of artifacts is obtained.

Although modifications and changes may be suggested by those skilled in the art it is the intention of the inventor to embody within the patent warranted hereon all changes and modifications as reasonably and properly come within the scope of his contribution to the art.

I claim as my invention:

1. A shock wave source for disintegrating a calculus in a patient comprising:
    a housing;
    means in said housing for generating shock waves in a propagation direction;
    means in said housing following said means for generating shock waves in said propagations direction and adapted for coupling said shock waves to a patient, said means for planar coupling having a coupling surface 8 adapted for pressing flush against a patient, said planar coupling surface 9 having a coupling surface normal substantially parallel to the shock wave propagation direction when pressed flush against said patient; and
    ultrasound means for locating and observing a calculus in said patient, said ultrasound means including an ultrasound head centrally disposed in said means for generating shock waves and having an ultrasound exit face with an exit face surface normal always disposed obliquely relative to said coupling surface normal.

2. A shock wave source as claimed in claim 1, wherein said ultrasound exit face of said ultrasound head is planar.

3. A shock wave source as claimed in claim 2, wherein said ultrasound head is formed by a transducer array adapted for operation as a linear array.

4. A shock wave source as claimed in claim 2, wherein said ultrasound head is formed by a transducer array adapted for operation as a phased array.

5. A shock wave source as claimed in claim 1, wherein said ultrasound exit face of said ultrasound head is conical.

6. A shock wave source as claimed in claim 1, wherein said ultrasound head is an annular array.

7. A shock wave source as claimed in claim 1, further comprising means for mounting said ultrasound head for pivoting around an axis.

8. A shock wave source as claimed in claim 7, wherein said means for generating shock waves has a central axis extending in said direction of propagation of said shock waves, and wherein said means for mounting is so that said axis around which said ultrasound head pivots is disposed perpendicularly relative to said central axis.

9. A shock wave source as claimed in claim 8, wherein said ultrasound exit face is a conical surface having a tip and a base, and wherein said pivot axis lies in a circular sectional surface between said base and said tip.

10. A shock wave source as claimed in claim 8, wherein said ultrasound exit face is a conical surface having a tip and a base and wherein said pivot axis lies in a circular sectional surface coincident with said base.

11. A shock wave source as claimed in claim 8, further comprising means for mounting said ultrasound head for rotation around a further axis, said further axis being perpendicular to a surface containing said central pivot axis and said axis.

12. A shock wave source as claimed in claim 1, wherein said housing encompasses a centrally disposed volume substantially free of shock waves, and wherein said ultrasound head is disposed in said volume.

13. A shock wave source as claimed in claim 1, wherein said ultrasound head has an annular transducer array disposed on a conical surface comprising the ultrasound exit face of the ultrasound head.

14. A shock wave source as claimed in claim 1, wherein said ultrasound exit face is planar, wherein said means for generating shock waves has a central axis extending in said direction of propagation of shock waves, and further comprising means for mounting said ultrasound head for pivoting around an axis substantially parallel to said planar exit face such that said ultrasound head is titled so that an exit face surface normal is disposed obliquely relative to said central axis.

15. A shock wave source as claimed in claim 14 wherein said ultrasound head includes a linear transducer array consisting of a plurality of transducers arranged successively side-by-side separated by spaces in the direction of said axis around which said ultrasound head pivots.

16. A shock wave source as claimed in claim 14 wherein said ultrasound head includes an annular array consisting of a plurality of annular, concentric transducers having respectively different diameters disposed on said planar exit face.

* * * * *